(12) United States Patent
Campbell et al.

(10) Patent No.: US 9,175,323 B2
(45) Date of Patent: *Nov. 3, 2015

(54) PROCESS FOR TREATING BIOMASS

(71) Applicant: THE MICHIGAN BIOTECHNOLOGY INSTITUTE, Lansing, MI (US)

(72) Inventors: Timothy J. Campbell, East Lansing, MI (US); Farzaneh Teymouri, Okemos, MI (US)

(73) Assignee: THE MICHIGAN BIOTECHNOLOGY INSTITUTE, Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,481

(22) PCT Filed: Apr. 24, 2013

(86) PCT No.: PCT/US2013/037935
§ 371 (c)(1),
(2) Date: Oct. 9, 2014

(87) PCT Pub. No.: WO2013/163271
PCT Pub. Date: Oct. 31, 2013

(65) Prior Publication Data
US 2015/0068516 A1    Mar. 12, 2015

Related U.S. Application Data (63) Continuation of application No. 13/458,568, filed on Apr. 27, 2012, now Pat. No. 9,102,964.

(51) Int. Cl.
| | |
|---|---|
| *D21C 1/06* | (2006.01) |
| *C12P 19/00* | (2006.01) |
| *C12P 19/14* | (2006.01) |
| *C12P 19/02* | (2006.01) |
| *C12P 7/10* | (2006.01) |
| *D21C 1/02* | (2006.01) |
| *D21C 5/00* | (2006.01) |

(52) U.S. Cl.
CPC . *C12P 19/14* (2013.01); *C12P 7/10* (2013.01); *C12P 19/00* (2013.01); *C12P 19/02* (2013.01); *D21C 1/02* (2013.01); *D21C 1/06* (2013.01); *C12P 2201/00* (2013.01); *D21C 5/005* (2013.01); *Y02E 50/16* (2013.01); *Y02E 50/343* (2013.01)

(58) Field of Classification Search
CPC ......... Y02E 50/16; Y02E 50/343; C12P 7/10; C12P 19/00; C12P 19/02; C12P 19/14; C12P 2201/00; D21C 1/06; C08B 1/003
See application file for complete search history.

(56) References Cited

U.S. PATENT DOCUMENTS

| | | | |
|---|---|---|---|
| 4,287,162 | A | 9/1981 | Scheibel |
| 5,171,592 | A | 12/1992 | Holtzapple et al. |
| 7,537,744 | B2 | 5/2009 | Benderly et al. |
| 7,915,017 | B2 | 3/2011 | Dale |
| 7,937,851 | B2 | 5/2011 | Rajagopalan et al. |
| 8,030,030 | B2 | 10/2011 | Varanasi et al. |
| 2008/0229657 | A1 | 9/2008 | Senyk et al. |
| 2011/0192559 | A1 | 8/2011 | Venkatesh et al. |
| 2011/0290114 | A1 | 12/2011 | Campbell et al. |
| 2013/0289268 | A1* | 10/2013 | Teymouri et al. ............. 536/124 |

FOREIGN PATENT DOCUMENTS

| | | |
|---|---|---|
| WO | WO-2007/130337 | 11/2007 |
| WO | WO-2008/114139 | 9/2008 |

OTHER PUBLICATIONS

Sendich et al., "Recent Process Improvements for the Ammonia Fiber Expansion (AFEX) Process and Resulting Reductions in Minimum Ethanol Selling Price," *Bioresource Technology*, 99:8429-35 (2008).
Bals et al., "Evaluating the Impact of Ammonia Fiber Expansion (AFEX) Pretreatment Conditions on the Cost of Ethanol Production," *Bioresource Technology*, 102:1277-83 (2011).
International Search Report in PCT/US2013/037935, mailed on Jul. 19, 2013 (5 pages).
Written Opinion of the International Searching Authority in PCT/US2013/037935, mailed on Jul. 19, 2013 (5 pages).

* cited by examiner

*Primary Examiner* — David M Brunsman
(74) *Attorney, Agent, or Firm* — Marshall, Gerstein & Borun LLP (57) ABSTRACT

This invention is directed to a process for treating biomass. The biomass is treated with a biomass swelling agent within the vessel to swell or rupture at least a portion of the biomass. A portion of the swelling agent is removed from a first end of the vessel following the treatment. Then steam is introduced into a second end of the vessel different from the first end to further remove swelling agent from the vessel in such a manner that the swelling agent exits the vessel at a relatively low water content.

89 Claims, 3 Drawing Sheets

PROCESS FOR TREATING BIOMASS

STATEMENT REGARDING FEDERALLY SPONSORED RESEARCH OR DEVELOPMENT

This invention was made with Government support under Cooperative Agreement No. DE-EE0005071 awarded by the United States Department of Energy. The Government has certain rights in the invention.

FIELD OF THE INVENTION

This invention relates to a process for treating biomass using a swelling agent. In particular, this invention relates to a process for treating biomass using a swelling agent and recovering a substantial portion of the swelling agent in relatively pure form.

BACKGROUND OF THE INVENTION

Biomass is generally composed of cellulose, hemicellulose, and lignin. The cellulose portion of biomass is particularly desirable in that this portion can be converted into individual sugar components, which can then be converted by microorganisms into various useful chemical compounds. As one example, the individual sugar components can be converted by microorganisms into ethanol, which can be used as a fuel or fuel additive for combustion engines.

The cellulose and hemicelluloses portions of the biomass are tightly bound to the lignin. Unless the cellulose and hemicelluloses are at least somewhat unbound from the lignin, conversion to individual sugar components, and into various chemicals by microbial action, can be highly inefficient. Biomass treatment processes such as dry milling, wet milling, steam explosion and ammonia fiber expansion (AFEX™—pending use and registration by MBI), however, have been used to unbind or break apart the various portions of the biomass, and thereby increase efficiency of conversion to individual sugar components, and ultimately to the various chemicals produced by microbial action.

U.S. Pat. No. 7,915,017 (Dale), for example, discloses a biomass treatment process that renders the structural carbohydrates of the biomass more accessible and/or digestible. The process uses ammonia to swell or rupture the biomass. The ammonia is recovered as ammonia vapor from an ammonia column, ultimately recycling the recovered ammonia in relatively dry form.

U.S. Pat. No. 5,171,592 (Holtzapple) discloses an ammonia biomass treatment process. The process includes recovery and recycle of the ammonia using superheated ammonia vapor to strip residual ammonia from the treated biomass.

AFEX™ type processes have been found to be quite effective in treating biomass. However, recovery of the various swelling agents used in those processes have been less than desirable in that substantial steps have been involved to recover the swelling agents for reuse. In order to increase efficiencies of the overall treatment process, it is therefore desirable to increase the efficiency of recovery and reuse of the swelling agents.

SUMMARY OF THE INVENTION

This invention provides a process for treating biomass that is highly effective in treating the biomass. The invention includes the use of a swelling agent as a treatment agent. The overall treatment process is highly efficient and is particularly efficient in the recovery and reuse of the swelling agent. The swelling agent can be recovered in a relatively pure form such that downstream processing and/or recovery of the swelling agent for recycle is minimal.

According to one aspect of this invention, there is provided a process for treating biomass. The process comprises a step of treating the biomass with a biomass swelling agent within a vessel to swell or rupture at least a portion of the biomass. At least a portion of the swelling agent is removed from a first end of the vessel, while leaving at least a majority of the treated biomass within the vessel. The treated biomass left within the vessel is then contacted with steam, which is introduced into a second end of the vessel different from the first end, to further remove swelling agent from the vessel.

In one embodiment, the contact of the steam and the treated biomass in the vessel is carried out such that the vessel is at a bed angle of not greater than 30 degrees from vertical.

Alternatively, the biomass is contained within the vessel at a bed porosity of at least 85 vol %.

Numerous swelling agents can be used according to this invention. One example of an effective swelling agent is a nitrogen containing composition, e.g., ammonia.

The swelling agent is added to the vessel in a quantity that will swell or rupture the biomass. For example, the swelling agent can be added to provide a weight ratio of swelling agent to biomass in a contacting zone of the vessel of at least 0.1:1.

In another embodiment of the invention, the contact of the steam and the treated biomass in the vessel is carried out based on a desired or predetermined Archimedes number. For example, the contact of the steam and the treated biomass in the vessel can be carried out to provide an Archimedes number of at least 4.

The swelling agent is removed from the vessel at a low water content. For example, the swelling agent can be removed from the vessel in a first step by a letting down pressure in the vessel and a second step of contacting the biomass with steam, with the recovered swelling agent having a low water content. The swelling agent can be removed and recovered directly from the treatment vessel during the steam contacting step. The directly recovered swelling agent can have a water content of not greater than 15 wt %, based on total content of swelling agent recovered during the steam contacting step. The swelling agent can be removed directly from the vessel as a vapor.

The contact zone of the vessel preferably has a length greater than its width. For example, the biomass can be contained within a contact zone of the vessel such that the contact zone has a length to diameter ratio of greater than four.

Contacting or stripping steam can be supplied to the vessel over a wide range of temperatures and pressures. In other words, the steam supplied to the vessel to remove residual swelling agent can be saturated or superheated steam.

The biomass is treated with the swelling agent in a manner that swells or ruptures the biomass, leaving a biomass that can be more easily digested by enzyme action. For example, the biomass can be treated with swelling agent to increase enzyme digestibility by at least 10% relative to that initially supplied to the vessel.

BRIEF DESCRIPTION OF THE DRAWINGS

Examples of various preferred embodiments of this invention are shown in the attached Figures, wherein.

DETAILED DESCRIPTION OF THE INVENTION

I. Overall Process for Treating Biomass

This invention relates to a process for treating biomass, i.e., cellulosic biomass, using a swelling agent. Treating the biomass with the swelling agent increases the chemical and biological reactivity of biomass for subsequent processing. For example, contacting the biomass with the swelling agent can cause the biomass to swell or rupture, increasing the chemical and biological reactivity of the biomass for subsequent processing.

The invention represents a significant improvement over known treatment processes by effectively recovering the swelling agent directly from the treatment vessel and recycling the swelling agent for reuse. The invention is particularly effective in that the swelling agent can be recovered in substantially pure vapor form, i.e., little to no moisture or water content, when steam is used as a driving force to evacuate the treatment vessel of residual swelling agent following treatment of the biomass with the swelling agent to swell and/or rupture at least a portion of the biomass.

II. Biomass

Biomass refers to living and recently dead biological material that can be used as fuel or for industrial production. Generally, biomass refers to plant matter grown for use as biofuel, but it also includes plant or animal matter that can be used for production of fibers, chemicals or heat. Biomass may also include biodegradable wastes that can be burned as fuel. It excludes organic material which has been transformed by geological processes into substances such as coal or petroleum.

Particularly suitable biomass includes such plant matter containing a relatively high content of cellulose. Examples of such biomass or plant matter include miscanthus, switchgrass, wheat straw, rice straw, oat hulls, hemp, corn (e.g., stover or cob), poplar, willow, sugarcane and oil palm (palm oil). Even municipal wastes such as newspaper can all be used as suitable biomass material.

Other examples of biomass include stems, leaves, hulls, husks, wood, wood chips, wood pulp, and sawdust. Particular examples of paper waste include discard photocopy paper, computer printer paper, notebook paper, notepad paper, typewriter paper, newspapers, magazines, cardboard, and paper-based packaging materials.

In one embodiment, the biomass is predominantly one or more $C_4$ grasses. $C_4$ grasses are classified by their pathway of carbon dioxide metabolism, which involves intermediates with 4 carbon atoms. This is described in *Biology of Plants*, by Raven, Evert, and Curtis, Worth Publishing Co., second edition, 1976, pages 116-117, incorporated herein by reference. Particularly preferred $C_4$ grasses are $C_4$ perennial grasses. Perennial grasses do not require yearly planting and fertilization and are therefore more suitable for fermentation and ethanol production than annual grasses. Particularly preferred $C_4$ perennial grasses include switchgrass, miscanthus, cord grass, and rye grass. These grasses are particularly fast growing. Cord grass is classified as a $C_4$ grass even though a portion of its growth cycle uses $C_3$ metabolism.

III. Swelling Agent

The swelling agent is a chemical composition effective in swelling and/or rupturing at least a portion of the biomass in the contact or treatment zone of a vessel. The treated biomass is a highly desirable feed for fermentation, as the treated biomass will have a significant amount of cellulose available for fermentation compared to the untreated biomass. Fermentation can be anaerobic (deficient in oxygen) as well as aerobic (oxygenated). Under aerobic conditions, microorganisms such as yeast cells can break down sugars to end products such as $CO_2$ and $H_2O$. Under anaerobic conditions, yeast cells utilize an alternative pathway to produce $CO_2$ and ethanol. The feinientation reaction of the present invention is preferably anaerobic, i.e., partially or completely deficient in oxygen. Fermentation can also be used to refer to the bulk growth of microorganisms on a growth medium where no distinction is made between aerobic and anaerobic metabolism.

As a part of the fermentation process, the treated biomass can be contacted with one or more cellulase enzymes in an aqueous mixture. The cellulase can be provided as a purified enzyme or can be provided by a cellulase-producing microorganism in the aqueous mixture. Cellulase can include any enzyme that effects the hydrolysis or otherwise solubilizes cellulose (including insoluble cellulose and soluble products of cellulose). Suitable sources of cellulase include such commercial cellulase products as Spezyme™ CP, Cytolase™ M104, and Multifect™ CL (Genencor, South San Francisco, Calif.).

Examples of swelling agents include but are not limited to: 1) water soluble amines having the structure $NRR^1R^2$ where R, $R^1$ and $R^2$ are either the same or different and are selected from the group consist of H or hydrocarbons containing 1-20 carbons (alternatively 1-10 carbons or 1-8 carbons or 1-6 carbons), optionally substituted with oxygen, nitrogen, sulfur or phosphorous, or where two or more of the R groups are attached to form a cyclic group (particular examples include ammonia, methyl amine, dimethylamine, N-methyl, ethylamine, tripropylamine, and morpholine); 2) water soluble ammonium ions having the structure $+NRR^1R^2R^3$ where R, $R^1$, $R^2$ and $R^3$ are either the same or different and are selected from the group consisting of H or hydrocarbons containing 1-20 carbons (alternatively 1-10 carbons or 1-8 carbons or 1-6 carbons), optionally substituted with oxygen, nitrogen, sulfur or phosphorous, or where two or more of the R groups are attached to form a cyclic group (particular examples include, ammonium hydroxide, ammonium chloride, and trimethylammonium chloride); 3) hydroxides, carbonates, and bicarbonates of lithium, sodium, potassium, magnesium, and calcium, such as sodium hydroxide, magnesium carbonate, and calcium carbonate (lime); 4) water soluble mono, or poly carboxylic acids containing 1-20 carbons (alternatively 1-10 carbons or 1-8 carbons or 1-6 carbons) such as carbonic, acetic, trifloroacetic, succinic and citric; 5) inorganic acids such as sulfuric, sulfurous, nitric, nitrous, phosphoric, and hydrochloric, including agents that form inorganic acids when dissolved in water such as sulfur dioxide, which forms sulfurous acid when dissolved in water.

In one example, the swelling agent is in vapor form at one atmosphere pressure. In particular, the swelling agent is a vapor at one atmosphere pressure, and at least some portion (e.g., at least 20 wt % or at least 40 wt % or at least 60 wt %) of the swelling agent is a liquid within the vessel as the swelling or rupturing phase of the process is carried out.

The amount of swelling agent for treating the biomass can depend on the particular swelling agent used, with the particular biomass being treated having an effect in some cases as well. In general, the amount of swelling agent added to the treatment portion of the vessel is at a level sufficient to swell and/or rupture a desired portion of the biomass. For example, swelling agent is added to the vessel to provide a weight ratio of swelling agent to biomass in the treatment portion of the vessel of at least 0.1:1; alternatively from 0.1:1 to 10:1, or from 0.1:1 to 5:1.

IV. Vessel

The biomass can be treated in any vessel suitable for contacting the biomass with vapor and liquid compositions in order to effectively swell and/or rupture the biomass. Preferably, the vessel is a tube or hollow cylinder. In a particular embodiment, the vessel is a tube or hollow cylinder having ports located near its axis at either end to permit flow of influent and effluent gas and/or liquid streams.

In one embodiment of the invention, the vessel has an internal axial length greater than its internal diameter. For example, the vessel can have an internal axial length at least four times greater than its internal diameter, alternatively at least eight times greater than its internal diameter, or at least ten times greater than its internal diameter, or at least twelve times greater than its internal diameter.

The vessel can be arranged as part of a batch or continuous process system. There can be only one vessel, although more than one vessel can be used. In embodiments that incorporate more than one vessel in which biomass material is contained, the vessels can be arranged in parallel or series.

V. Process Conditions

Biomass material can be retained as a static or moving bed within the vessel. In the form of a static bed, the biomass can be retained by means of a permeable support, such as support mesh or screens fitted at the influent and effluent ends of the vessel. Mesh or screens with openings smaller than the biomass particles, preferably at least five times smaller, and most preferably at least ten times smaller, are used. At each end of the vessel, a plenum is preferably provided to allow for even gas flow distribution throughout the bed of biomass particles.

The biomass material is preferably arranged in the vessel as a porous packed bed. In this arrangement, the biomass is in particulate form, in which each particle is fixed in position relative to one another.

The biomass is also arranged in the vessel such that it is effectively treated with the swelling agent to cause the biomass to swell and/or rupture. The biomass is also arranged in the vessel such that the swelling agent can be removed with steam in such an manner that the swelling agent can be recovered directly from the vessel with little to no water content.

A variety of parameters can be used to ensure appropriate removal of a low moisture content swelling agent from the vessel following treatment of the biomass in the vessel. An example of one such parameter is Archimedes number. The Archimedes number ($N_{Ar}$) quantifies the ratio of free to forced convection in a fluid system. $N_{Ar}$ is a useful parameter for controlling steam flow rate at levels that permit recovery of the swelling agent as substantially pure vapor, i.e., little to no moisture content. The value of $N_{Ar}$, calculated from measurable quantities as described below, indicates the relative strengths of free and forced convection within the mass transfer zone of the bed of biomass particles, which determines the fraction of residual swelling agent that may be recovered as substantially pure vapor.

$N_{Ar}$ can be calculated from Reynolds number ($N_{Re}$) and Grashof number ($N_{Gr}$) as:

$$N_{Ar}=N_{Gr}/N_{Re}^2.$$

For a cylindrical porous packed bed with circular cross section, the Grashof number ($N_{Gr}$) can be calculated from the bed diameter $D_{Bed}$ and bed angle $\theta_{Bed}$, the steam and vapor temperatures $T_{steam}$ and $T_{vap}$, densities $\rho_{steam}$ and $\rho_{vap}$, and viscosities $\mu_{steam}$ and $\mu_{vap}$, and the gravitational constant g=9.81 m/s² as:

$$N_{Gr}=[2gD_{Bed}^3(\rho_{steam}+\rho_{vap})^2(T_{steam}-T_{vap})\cos(\theta_{Bed})]/[(T_{steam}+T_{vap})(\mu_{steam}+\mu_{vap})^2].$$

For axial steam flow through a cylindrical porous packed bed with circular cross section, the Reynolds number ($N_{Re}$) can be calculated from the bed diameter $D_{Bed}$, the steam mass flow rate $m_{steam}$, and steam dynamic viscosity $\mu_{steam}$ as:

$$N_{Re}=(4m_{steam})/(\pi\mu_{steam}D_{Bed}).$$

Bed porosity ($\epsilon_{Bed}$, volume %) may be calculated using the bed density $\rho_{Bed}$ and the biomass true density $\rho_{True}$, as $\epsilon_{Bed}=100(1-\rho_{Bed}/\rho_{True})$. In one embodiment, biomass particles are included in the treatment vessel at a bed porosity of at least 85 vol %, alternatively at least 88 vol %.

Biomass bed density ($\rho_{Bed}$, kg/m³) may be calculated as $\rho_{Bed}=m_{Bed}/V_{Bed}$, where $V_{Bed}$ is the bed volume (m³) calculated from the bed dimensions using a suitable geometric formula.

Biomass bed dry mass ($m_{Bed}$, kg) can be calculated from $m_{total}$ and $x_{moist}$ as $m_{Bed}=m_{total}(1-x_{moist}/100)$.

Steam density ($\rho_{steam}$, kg/m³) and viscosity ($\mu_{steam}$, kg/m s) may be interpolated from standard literature steam table values using the measured steam temperature $T_{steam}$.

Figure 2:
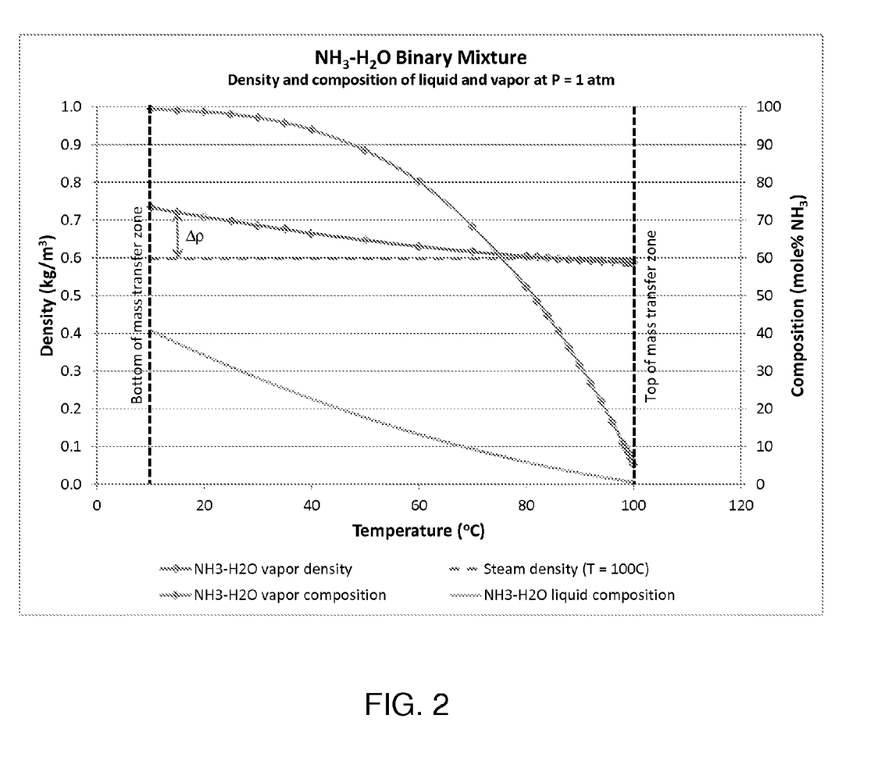
FIG. 2 is a standard ammonia-water binary mixture density-temperature-composition diagram, which can be used to determine Archimedes number of the treatment vessel in accordance with one embodiment of this invention.

Vapor composition, density ($\rho_{vap}$, kg/m³), and dynamic viscosity ($\mu_{vap}$, kg/m s) may be calculated from the vapor temperature $T_{vap}$ by interpolation using FIG. 2, or by comparison to literature data for properties of saturated ammonia-water vapor mixtures at the appropriate pressure Tillner-Roth, R., and D. G. Friend, "A Helmholtz free energy formulation of the thermodynamic properties of the mixture {water+ammonia}", J. Phys. Chem. Ref. Data, Vol. 27, no. 1, 1998, p 63-83, the contents of which are incorporated herein by reference.

"Steam mass rate ($m_{steam}$, kg/s)" refers to the mass of steam that is injected or input to the reaction or contact vessel. The steam mass rate may be measured using an appropriate flow meter, such as a vortex meter. Alternatively, the steam mass rate may be determined by measuring the composite moisture content of a biomass bed before and after steaming for a measured interval of time, during which negligible steam flow from the exit end of the bed is observed.

"Steam and vapor temperatures ($T_{steam}$ and $T_{vap}$, K)" refer to steam temperature at the entrance of the reaction or contact vessel and temperature of swelling agent exiting from the reaction or contact vessel, with the swelling agent exiting from the vessel substantially in the vapor phase. The steam and vapor temperatures may be measured using temperature sensors positioned in the inlet steam and exit streams no more than one bed diameter from the inlet and exit ends of the bed, respectively.

The steam that is used as the driving force to evacuate the treatment vessel of residual swelling agent can be saturated or superheated. The steam pressure will depend upon the pressure rating of the treatment vessel. As an example, steam pressures of from 5 psig to 500 psig can be used. Alternatively steam pressures from 5 psig to 400 psig or from 5 psig to 300 psig can be applied.

"Biomass true (skeletal) density ($\rho_{True}$, kg/m$^3$)" refers to the true density of biomass in the reaction portion of a vessel, which may be measured by volumetric pycnometry analysis. True density values were measured using an automatic gas pycnometer instrument (Quantachrome Pentapyc 5200e) following the standard methods.

"Bed angle ($\theta_{Bed}$)" refers to the angle between the direction of axial flow through the biomass bed and the local gravity vector. $\theta_{Bed}$ may be conveniently measured using a carpenter's plumb line or spirit level. In one embodiment, the bed angle is not greater than 30 degrees from vertical, alternatively not greater than 25 degrees from vertical, or not greater than 20 degrees from vertical.

"Biomass moisture content ($x_{moist}$, mass %)" refers to the water content of the biomass in the vessel, and may be measured thermo-gravimetrically as loss on drying at 105° C., as described in Ehrman, T., "Standard method for determination of total solids in biomass", NREL Laboratory Analytical Procedure LAP-001, National Renewable Energy Laboratory, Golden, Colo., November 1994, the contents of which are incorporated herein by reference.

"Biomass total bed mass ($m_{total}$, kg)" refers to total biomass in the reaction portion of a vessel (i.e., zone in which biomass is treated), and may be measured by gravimetrically measuring the difference between the full and tare masses of a container to be assembled as the bed in the vessel. Equivalently, $m_{total}$ may be measured as the difference between the full and tare masses of a bin from which biomass is transferred with minimal mass loss into the reaction portion of the vessel.

In order to remove and recover swelling agent from the treated biomass at the desired moisture content, the Archimedes number should be high enough so that the recovered swelling agent can be recycled for reuse, with little to no processing, since the recovered swelling agent is in a highly pure form. For example, Archimedes number can be at least 4, alternatively at least 4.5, or at least 5.

The swelling agent can be recovered from the reactor or treatment vessel with very little water. For example, the swelling agent can be recovered directly from the treatment vessel following biomass treatment and steam contacting or stripping at a water content of not greater than 10 wt %, alternatively not greater than 5 wt % water, alternatively not greater than 3 wt % water, or not greater than 1 wt % water, based on total weight of swelling agent recovered directly from the treatment vessel following biomass treatment and steam contacting or stripping. The swelling agent can be also be recovered directly from the treatment vessel, and during the steam contacting or stripping step, at a water content of not greater than 15 wt %, alternatively not greater than 10 wt % water, or not greater than 5 wt % water, based on total weight of swelling agent recovered directly from the treatment vessel during steam contacting or stripping. The swelling agent can be recovered directly from the vessel as a vapor.

The temperature and pressure of the vessel during treatment of the biomass with the swelling agent are sufficiently high to enhance swelling and/or rupturing of the biomass. When a swelling agent is used that is a vapor at standard conditions, i.e., one atmosphere and 25° C., it is preferred to maintain the temperature and pressure of the vessel such that at least a portion of the swelling agent is in liquid phase as the swelling or rupturing phase of the process is carried out.

In one embodiment of the invention, the process is carried out such that the vessel containing the biomass is within a temperature range of from 25° C. to 200° C. Preferably, the process is carried out such that the temperature of the vessel containing the biomass is within a range of from 30° C. to 180° C., more preferably from 50° C. to 150° C.

In another embodiment of the invention, the process is carried out such that the pressure of the vessel during treatment of the biomass with the swelling agent is within a range of from 20 psia (137.9 kPaa) to 1000 psia (6895 kPaa). Preferably, the treatment portion of the process is carried out such that the pressure of the vessel containing the biomass being treated is within a range of from 40 psia (275.8 kPaa) to 800 psia (5516 kPaa), more preferably from 60 psia (413.7 kPaa) to 500 psia (3447 kPaa).

The biomass is contacted or treated with the swelling agent for a time that is sufficient to swell and/or rupture at least a portion of the biomass. For example, the biomass can be contacted or treated with swelling agent to swell and/or rupture at least 25 wt % of the biomass material or at least 50 wt % of the biomass material. The biomass can be contacted with swelling agent for at least one minute, alternatively for at least two minutes, or at least five minutes.

VI. Removing Swelling Agent

Following treatment of the biomass with the swelling agent, at least a portion of the swelling agent is removed from a first end of the vessel, while leaving at least a majority of the treated biomass within the vessel. The treated biomass left within the vessel is then contacted with steam that is introduced into a second end of the vessel different from the first end to remove at least a portion of residual swelling agent, i.e., swelling agent that has not been absorbed into the biomass, remaining in the vessel.

The swelling agent can be removed from the vessel following treatment by opening the first end of the vessel in a manner that reduces pressure within the vessel. For example, a valve can be placed in a line from the first end of the vessel such that the valve can be opened as desired to remove swelling agent from the treated biomass. As a particular example, the pressure of the vessel can be reduced to less than 50% of the pressure of the vessel during treatment with the swelling agent. Alternatively, the pressure of the vessel can be reduced to less than 20% or less than 10% of the pressure of the vessel during treatment with the swelling agent, in order to remove swelling agent from the treated biomass in the vessel.

Residual swelling agent can remain in the vessel following the opening of the first end of the vessel to remove swelling agent from the vessel. This residual swelling agent can then be removed by injecting steam into the second end of the vessel. This injection is carried out under the conditions as described above in order to recover a substantial portion of the swelling agent in relatively pure or dry form.

As the steam is injected into the second end of the vessel, the first end of the vessel can be monitored to determine the quality of the stream exiting the second end. For example, the stream exiting the vessel can be monitored to determine the content of the swelling agent and moisture level of the stream exiting the vessel as the steam is applied at the second end of the vessel. As long as the stream exiting the vessel is at an acceptably low moisture content, the stream can be recovered for re-use as the recovered stream will be highly pure swelling agent.

VII. Further Processing of Biomass

In certain embodiments of the invention, the treated biomass material can be further processed or otherwise chemically converted. For example, the biomass material can be removed following steam application to remove residual swelling agent from the vessel, and then be used to produce chemical derivates such as to make ethanol or other compositions useful as transportation fuel or fuel components. In such an example, the biomass material can be fermented to produce the desired fuel components.

In a preferred embodiment of the invention, the swelling agent can sufficient treat the biomass material to increase enzyme digestibility of the biomass. Enzyme digestibility refers to the ability of the biomass material to be converted into its constituent sugar components by hydrolytic enzymes. According to this invention, enzyme digestibility is measured using a standard laboratory protocol. See, e.g., "Enzymatic saccharification of lignocellulosic biomass," National Renewable Energy Laboratory Technical Report TP-510-42629, March 2008.

For the purposes of this invention, enzyme digestibility is the rate at which a biomass material may be digested to one or more of glucose and xylose using cellulase or xylanase enzymes. The quantitative effect of contact or treatment of the biomass material with the swelling agent with regard to the enzyme digestibility of the biomass material can be measured by adding 0.15 grams dry mass of biomass sample that has been contacted or treated with the swelling agent to a glass scintillation vial, and the same dry mass of biomass that has not been contacted or treated to a separate vial. Preferably, duplicate vials of both biomass samples are prepared.

To each vial is then added 5.0 milliliters of 0.1 molar pH 4.8 sodium citrate buffer, and a quantity of cellulase enzyme solution equal to 1.5 Filter Paper Units (FPU) of activity. An equal quantity of xylase enzyme can also be added to each vial.

The total volume in each vial is then diluted to 10.0 milliliters by adding distilled water. The vials are then sealed and incubated at 50±1° C., with sufficient agitation to keep the solids suspended, for 48 hours. Conditions during the incubation period, including temperature and pH, can be adjusted as necessary to suit the particular enzymes used in digestion.

After incubation, a liquid aliquot is drawn from each vial and filtered through a 0.45 micron filter, and the filtrate is then analyzed to determine the concentration of glucose, xylose, or both using HPLC or any other suitable quantitative technique.

Increased enzyme digestibility of biomass can then be calculated as Xcell=100*[(CGlu)abs/(CGlu)−1], where Xcell is the percent increase in cellulose digestibility, (CGlu) abs the concentration of glucose in the filtrate from the biomass that has been contacted or treated with the swelling agent, and (CGlu) is the concentration of glucose in the filtrate from the biomass that has not been contacted or treated with the swelling agent.

A similar calculation can be performed for increased enzyme digestibility based on the concentrations of xylose in the filtrate aliquots. In such a case, Xcell=100*[(CXyl)abs/(CXyl)−1], where Xcell is the percent increase in xylan digestibility, (CXyl)abs is the concentration of xylose in the filtrate from the biomass that has been contacted or treated with the swelling agent, and (CXyl) is the concentration of xylose in the filtrate from the biomass that has not been contacted or treated with the swelling agent. Preferably, contact or treatment of the biomass material with the swelling agent increases enzyme digestibility by at least 5%, more preferably by at least 50%, and most preferably by at least 100%. This increase can be measured by one or more of an increase in cellulose and xylose digestibility as defined by Xcell.

In one embodiment of the invention, the biomass is treated with the swelling agent to increase enzyme digestibility by at least 10% relative to that initially supplied to the vessel. Alternatively, the biomass is treated with the swelling agent to increase enzyme digestibility by at least 20%, more preferably at least 30%, and most preferably at least 40%, relative to that initially supplied to the vessel.

VIII. EXAMPLES

Figure 1:
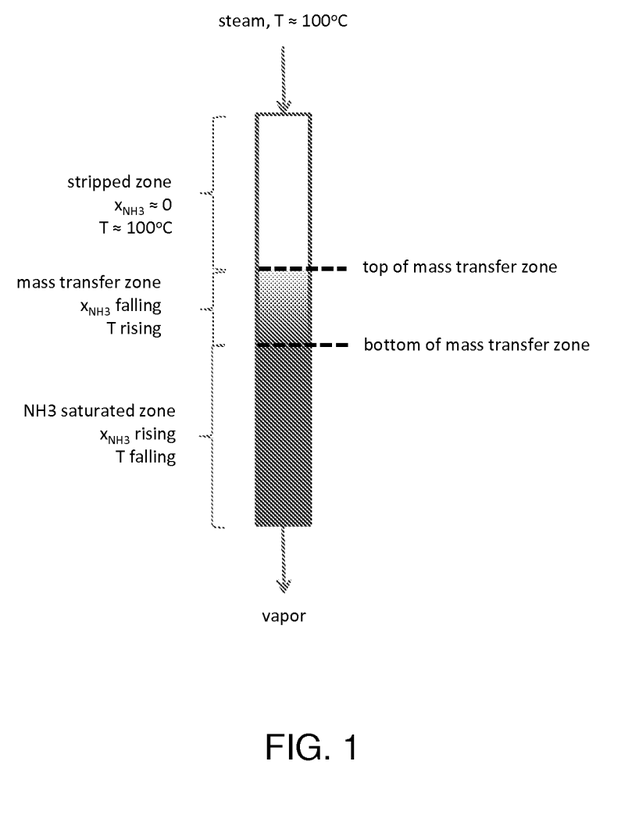
FIG. 1 is a simple flow diagram of one embodiment of recovering swelling agent as a vapor, in which the swelling agent vapor is exemplified as ammonia vapor.

FIG. 1 shows a flow diagram of recovery of swelling agent vapor, exemplified as ammonia vapor, in which ammonia vapor is expelled from the bottom of a vertical porous packed bed of biomass at atmospheric pressure, as steam is introduced to the top of the bed. At any point during the recovery process, the bed can be divided into three zones. At the top of the bed is a stripped zone, where swelling agent, i.e., $NH_3$, concentration is negligible and the bed temperature is about equal to that of the incoming steam. At the bottom of the bed is an $NH_3$ saturated zone into which steam has not yet penetrated, where $NH_3$ concentration is rising and bed temperature is falling due to absorption of $NH_3$-rich vapor flowing down from the sections above. Exiting the bottom of the $NH_3$ saturated zone is vapor whose composition is in equilibrium with the absorbed liquid in the saturated zone.

Between the stripped zone and the $NH_3$ saturated zone is a mass transfer zone, where steam is condensing, liberating heat that vaporizes ammonia from the absorbed liquid. Along the bottom edge of the mass transfer zone, the absorbed liquid is $NH_3$-rich, so that the vapor arising from the biomass is significantly colder and denser than the steam entering the top of the mass transfer zone. This density difference, between the hot steam and the colder vapor arising from the $NH_3$-rich biomass, may cause significant buoyant effects during the steam stripping process.

FIG. 2 shows the composition and density of vapor arising from biomass over the range of temperatures encountered during $NH_3$ recovery (data from Tillner-Roth, R., and D. G. Friend, "A Helmholtz free energy formulation of the thermodynamic properties of the mixture {water+ammonia}", J. Phys. Chem. Ref. Data, Vol. 27, no. 1, 1998, p 63-83). For reference, FIG. 2 also shows the density of saturated steam at atmospheric pressure. At the bottom of the mass transfer zone, the $NH_3$-rich vapor temperature can be less than 10° C., and the density difference $\Delta\rho$ between the incoming steam and the $NH_3$-rich vapor is significant, while at the top of the mass transfer zone the temperature approaches that of the steam, and $\Delta\rho$ approaches zero.

Steam is transported into the mass transfer zone by forced convection. Forced convective mixing of incoming steam with the $NH_3$-rich vapor arising from the biomass will increase the length of the mass transfer zone. The longer the mass transfer zone is relative to the length of the bed, the less will be the percentage of residual ammonia that can be recovered from the bed as substantially pure vapor. Free convection, driven by the density difference $\Delta\rho$ between the steam and the $NH_3$-rich vapor, will oppose forced convective mixing by segregating the steam from the $NH_3$-rich vapor, preventing lengthening of the mass transfer zone.

Examples 1-8

General Experimental

A series of experiments was carried out in which biomass was milled, screened and packed into six identical cylindrical containers, each 9.7 centimeters in diameter and 15 centimeters long. The containers were constructed with end plates made of perforated sheet with 41% open area to allow axial flow of vapor in and out of each container, and the biomass was compressed into the containers. The six containers were assembled into a vertical stainless steel tubular bed vessel 10.2 centimeters outer diameter and 125 centimeters long, with the end of each container in contact with the adjacent containers, forming a segmented porous bed 9.7 centimeters in diameter and 90 centimeters long.

The bed was pre-steamed by introducing steam at a mass flow rate of 1 gram per second into the top of the tube and allowing steam and displaced air to flow vertically downward out the bottom of the bed to vent for approximately ten minutes. The bed was then ammoniated by blocking flow from the bottom of the bed while introducing compressed anhydrous ammonia vapor to the top of the bed. Maximum pressure during ammoniation reached 200 psig. Ammonia was added until a ratio of 1:1 ammonia:dry biomass was achieved.

Following treatment of the biomass with the ammonia, the pressure was released from the bed by allowing vapor to flow out the bottom of the bed until the bed pressure was 1 atmosphere. The residual ammonia was then recovered from the bed by introducing steam at a mass flow rate of 1 gram per second into the top of the bed while allowing vapor to flow at atmospheric pressure from the bottom of the bed.

The temperature of the vapor expelled from the bottom of the bed was monitored using a temperature sensor positioned less than 10 centimeters from the bottom of the bed; the composition of the vapor was determined from the temperature by interpolation using the $NH_3$—$H_2O$ vapor composition curve in FIG. 2. The vapor was trapped in discrete citric acid fractions of known mass and concentration; the pH change was used to calculate the mass of ammonia trapped in each fraction.

Figure 3:
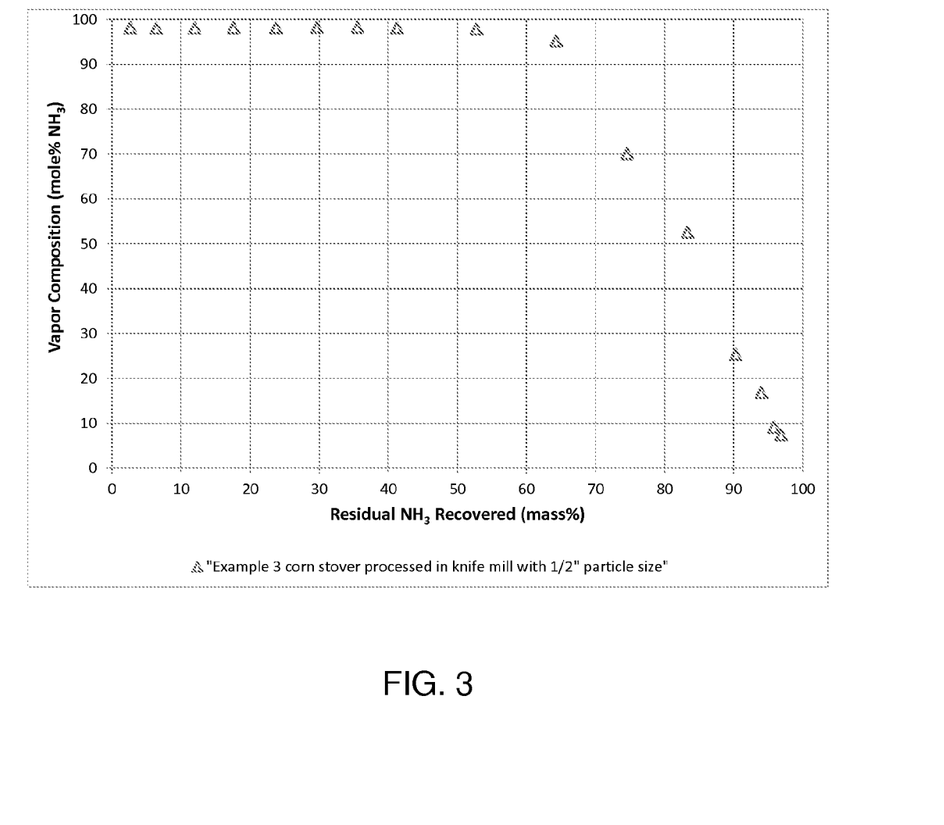
FIG. 3 is a plot of one example of the quality of recovery of swelling agent compared to the amount of swelling agent that can be recovered according to this invention.

The following Table provides the various biomass characteristics and operating conditions for each Example. Examples 1 and 2 are provided as comparative examples. Examples 3-8 represent one or more embodiments of the overall invention. As an example of quality of recovery compared to amount of swelling agent that can be recovered according to this invention, a plot of the composition of the vapor expelled during steam stripping and recovery of the residual ammonia from the bed for Example 3 is shown in FIG. 3.

porosity, Archimedes no., etc.) resulted in recovery of the ammonia at very high purity. The same would be expected for a variety of swelling agents, particularly swelling agents that are in the vapor phase at standard conditions, i.e., one atmosphere and 25° C. One benefit of recovering swelling agent at relatively high purity is that the swelling agent can be recycled with little to no downstream processing.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:

1. A process for treating biomass, comprising:
   treating the biomass with a biomass swelling agent within a vessel to swell or rupture at least a portion of the biomass;
   removing at least a portion of the swelling agent from a first end of the vessel, while leaving at least a majority of the treated biomass within the vessel; and
   contacting the treated biomass left within the vessel with steam introduced into a second end of the vessel different from the first end to further remove swelling agent from the vessel, wherein during the contact of the steam and the treated biomass in the vessel, the vessel is at a bed angle of not greater than 30 degrees from vertical.

2. The process of claim 1, wherein the biomass is contained within the vessel at a bed porosity of at least 85 vol %.

3. The process of claim 1, wherein the swelling agent is ammonia.

4. The process of claim 1, wherein swelling agent is added to the vessel to provide a weight ratio of swelling agent to biomass in a contacting zone of the vessel of at least 0.1:1.

5. The process of claim 1, wherein the contact of the steam and the treated biomass in the vessel is carried out to provide an Archimedes number of at least 4.

6. The process of claim 1, wherein the swelling agent that is removed from the vessel by contact with the steam is recovered directly from the treatment vessel during the steam contacting step, and the directly recovered swelling agent has a water content of not greater than 15 wt %, based on total content of swelling agent recovered during the steam contacting step.

TABLE

| | Ex. 1 | Ex. 2 | Ex. 3 | Ex. 4 | Ex. 5 | Ex. 6 | Ex. 7 | Ex. 8 |
| --- | --- | --- | --- | --- | --- | --- | --- | --- |
| Biomass type | Corn stover | Corn stover | Corn stover | Corn stover | Corn stover | Wheat straw | Wheat straw | Wheat straw |
| Mill, particle size | Knife, ½" | Knife, ½" | Knife, ½" | Hammer, 1" | Hammer, ½" | Knife, 4.7 mm | Knife, 8 mm | Knife, 30 mm |
| Bed angle ($\theta_{Bed}$, deg.) | 90 | 45 | 0 | 0 | 0 | 0 | 0 | 0 |
| Bed porosity ($\epsilon_{Bed}$, vol %) | 87 | 87 | 87 | 90 | 85 | 87 | 90 | 92 |
| Archimedes No. ($N_{Ar}$) | 0.0 | 3.8 | 5.8 | 5.8 | 5.8 | 6.1 | 6.1 | 6.1 |
| Residual $NH_3$ recovery (mass %) | 81 | 89 | 97 | 97 | 89 | 97 | 97 | 97 |
| $NH_3$ recovered during steam stripping containing >90% ammonia (mass %) | 28 | 34 | 64 | 91 | 43 | 69 | 85 | 89 |

As seen from the Examples, the experiments that were carried out within the desired parameters (e.g., bed angle, bed 7. The process of claim 6, wherein the swelling agent that is removed from the vessel is removed as a vapor.

8. The process of claim 7, wherein the swelling agent removed as vapor has a water content of not greater than 10 wt. %.

9. The process of claim 1, wherein the biomass is contained within a contact zone of the vessel, with the contact zone having a length to diameter ratio of greater than four.

10. The process of claim 1, wherein the steam is supplied to the vessel as saturated or superheated steam.

11. The process of claim 1, wherein the biomass is treated with the swelling agent to increase enzyme digestibility by at least 10% relative to that initially supplied to the vessel.

12. The process of claim 1, wherein during the contact of the steam and the treated biomass in the vessel, the vessel is at a bed angle of not greater than 20 degrees from vertical.

13. The process of claim 1, wherein the swelling agent comprises a water-soluble amine having the structure $NRR_1R_2$ where R, $R_1$ and $R_2$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

14. The process of claim 13, wherein the water-soluble amine is selected from the group consisting of ammonia, methylamine, dimethylamine, ethylamine, tripropylamine, morpholine, and mixtures thereof.

15. The process of claim 1, wherein the swelling agent comprises water-soluble ammonium ions having the structure $^+NRR_1R_2R_3$ where R, $R_1$, $R_2$, and $R_3$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

16. The process of claim 1, wherein the swelling agent comprises a hydroxide, carbonate, or bicarbonate of lithium, sodium, potassium, magnesium, or calcium.

17. The process of claim 1, wherein the swelling agent comprises a water soluble mono- or poly-carboxylic acid.

18. The process of claim 1, wherein the swelling agent comprises an inorganic acid.

19. The process of claim 1, wherein the vessel includes a plurality of containers within the vessel and positioned vertically relative to each other, each container comprising a perforated end plate and containing a portion of the biomass therein.

20. The process of claim 19, wherein the biomass in each container is compressed therein.

21. The process of claim 19, wherein the biomass is contained within the vessel at a bed porosity of at least 85 vol %.

22. The process of claim 1, further comprising:
recycling the swelling agent removed from the vessel to a second vessel containing biomass therein; and
contacting the biomass in the second vessel with the recycled swelling agent to swell or rupture at least a portion of the biomass.

23. The process of claim 22, wherein recycling the swelling agent comprises feeding the removed swelling agent to the second vessel with no processing to remove water when the removed swelling agent has a moisture content at or below a desired moisture content.

24. The process of claim 23, wherein the desired moisture content is 15 wt. %.

25. The process of claim 1, wherein removing at least a portion of the swelling agent from a first end of the vessel comprises, prior to introducing steam into the second end of the vessel, reducing pressure in the vessel to a value less than 50% of the pressure in the vessel during contacting the biomass with the swelling agent.

26. The process of claim 1, comprising performing removing at least a portion of the swelling agent and contacting the treated biomass left within the vessel with steam as a batch process.

27. The process of claim 1, comprising performing removing at least a portion of the swelling agent and contacting the treated biomass left within the vessel with steam as a continuous process.

28. The process of claim 1, comprising contacting the treated biomass left within the vessel with steam at a pressure from 5 psig to 500 psig.

29. The process of claim 1, comprising performing contacting the treated biomass left within the vessel at a temperature from 25° C. to 200° C.

30. The process of claim 1, further comprising pre-steaming the biomass in the vessel before treating the biomass with the swelling agent.

31. The process of claim 1, wherein the swelling agent is compressed vapor.

32. The process of claim 1, wherein the swelling agent is compressed ammonia.

33. The process of claim 1, wherein:
the swelling agent is ammonia, and
swelling agent is added to the vessel to provide a weight ratio of swelling agent to biomass in a contacting zone of the vessel of at least 0.1:1.

34. The process of claim 1, wherein:
the swelling agent is ammonia, and
the biomass is treated with the swelling agent to increase enzyme digestibility by at least 10% relative to that initially supplied to the vessel.

35. The process of claim 1, wherein:
the swelling agent that is removed from the vessel by contact with the steam is recovered directly from the treatment vessel during the steam contacting step, and the directly recovered swelling agent has a water content of not greater than 15 wt %, based on total content of swelling agent recovered during the steam contacting step,
the swelling agent that is removed from the vessel is removed as a vapor, and
the biomass is treated with the swelling agent to increase enzyme digestibility by at least 10% relative to that initially supplied to the vessel.

36. The process of claim 1, wherein:
the biomass is treated with the swelling agent to increase enzyme digestibility by at least 10% relative to that initially supplied to the vessel, and
the swelling agent comprises a water-soluble amine having the structure $NRR_1R_2$ where R, $R_1$ and $R_2$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

37. The process of claim 1, wherein:
the biomass is treated with the swelling agent to increase enzyme digestibility by at least 10% relative to that initially supplied to the vessel, and
the water-soluble amine is selected from the group consisting of ammonia, methylamine, dimethylamine, ethylamine, tripropylamine, morpholine, and mixtures thereof.

38. The process of claim 1, wherein:
the biomass is treated with the swelling agent to increase enzyme digestibility by at least 10% relative to that initially supplied to the vessel, and
the swelling agent comprises water-soluble ammonium ions having the structure $^+NRR_1R_2R_3$ where R, $R_1$, $R_2$, and $R_3$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

39. The process of claim 1, wherein:
the biomass is treated with the swelling agent to increase enzyme digestibility by at least 10% relative to that initially supplied to the vessel, and
the swelling agent comprises a hydroxide, carbonate, or bicarbonate of lithium, sodium, potassium, magnesium, or calcium.

40. The process of claim 1, wherein:
the biomass is treated with the swelling agent to increase enzyme digestibility by at least 10% relative to that initially supplied to the vessel, and
the swelling agent comprises a water soluble mono- or poly-carboxylic acid.

41. The process of claim 1, wherein:
the biomass is treated with the swelling agent to increase enzyme digestibility by at least 10% relative to that initially supplied to the vessel, and
the swelling agent comprises an inorganic acid.

42. The process of claim 1, wherein:
the biomass is treated with the swelling agent to increase enzyme digestibility by at least 10% relative to that initially supplied to the vessel, and
removing at least a portion of the swelling agent from a first end of the vessel comprises, prior to introducing steam into the second end of the vessel, reducing pressure in the vessel to a value less than 50% of the pressure in the vessel during contacting the biomass with the swelling agent.

43. The process of claim 1, wherein:
the contact of the steam and the treated biomass in the vessel is carried out to provide an Archimedes number of at least 4.5, and
the vessel includes a plurality of containers within the vessel and positioned vertically relative to each other, each container comprising a perforated end plate and containing a portion of the biomass therein.

44. The process of claim 1, wherein:
during the contact of the steam and the treated biomass in the vessel, the vessel is at a bed angle of not greater than 20 degrees from vertical, and
the vessel includes a plurality of containers within the vessel and positioned vertically relative to each other, each container comprising a perforated end plate and containing a portion of the biomass therein.

45. The process of claim 1, wherein:
the swelling agent is ammonia,
swelling agent is added to the vessel to provide a weight ratio of swelling agent to biomass in a contacting zone of the vessel of at least 0.1:1,
the swelling agent that is removed from the vessel by contact with the steam is recovered directly from the treatment vessel during the steam contacting step, and the directly recovered swelling agent has a water content of not greater than 15 wt %, based on total content of swelling agent recovered during the steam contacting step,
the steam is supplied to the vessel as saturated or superheated steam,
the biomass is treated with the swelling agent to increase enzyme digestibility by at least 10% relative to that initially supplied to the vessel, and
during the contact of the steam and the treated biomass in the vessel, the vessel is at a bed angle of not greater than 20 degrees from vertical.

46. A process for treating biomass, comprising:
treating the biomass with a biomass swelling agent within a vessel to swell or rupture at least a portion of the biomass;
removing at least a portion of the swelling agent from a first end of the vessel, while leaving at least a majority of the treated biomass within the vessel; and
contacting the treated biomass left within the vessel with steam introduced into a second end of the vessel different from the first end to further remove swelling agent from the vessel, wherein the contact of the steam and the treated biomass in the vessel is carried out to provide an Archimedes number of at least 4.

47. The process of claim 46, wherein the biomass is contained within the vessel at a bed porosity of at least 85 vol %.

48. The process of claim 46, wherein the swelling agent is ammonia.

49. The process of claim 46, wherein swelling agent is added to the vessel to provide a weight ratio of swelling agent to biomass in a contacting zone of the vessel of at least 0.1:1.

50. The process of claim 46, wherein the swelling agent that is removed from the vessel by contact with the steam is recovered directly from the treatment vessel during the steam contacting step, and the directly recovered swelling agent has a water content of not greater than 15 wt %, based on total content of swelling agent recovered during the steam contacting step.

51. The process of claim 50, wherein the swelling agent that is removed from the vessel is removed as a vapor.

52. The process of claim 51, wherein the swelling agent removed as vapor has a water content of not greater than 10 wt. %.

53. The process of claim 46, wherein the biomass is contained within a contact zone of the vessel, with the contact zone having a length to diameter ratio of greater than four.

54. The process of claim 46, wherein the steam is supplied to the vessel as saturated or superheated steam.

55. The process of claim 46, wherein the biomass is treated with the swelling agent to increase enzyme digestibility by at least 10% relative to that initially supplied to the vessel.

56. The process of claim 46, wherein during the contact of the steam and the treated biomass in the vessel, the vessel is at a bed angle of not greater than 20 degrees from vertical.

57. The process of claim 46, wherein the swelling agent comprises a water-soluble amine having the structure $NRR_1R_2$ where R, $R_1$ and $R_2$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

58. The process of claim 57, wherein the water-soluble amine is selected from the group consisting of ammonia, methylamine, dimethylamine, ethylamine, tripropylamine, morpholine, and mixtures thereof.

59. The process of claim 46, wherein the swelling agent comprises water-soluble ammonium ions having the structure $^+NRR_1R_2R_3$ where R, $R_1$, $R_2$, and $R_3$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

60. The process of claim 46, wherein the swelling agent comprises a hydroxide, carbonate, or bicarbonate of lithium, sodium, potassium, magnesium, or calcium.

61. The process of claim 46, wherein the swelling agent comprises a water soluble mono- or poly-carboxylic acid.

62. The process of claim 46, wherein the swelling agent comprises an inorganic acid.

63. The process of claim 46, wherein the vessel includes a plurality of containers within the vessel and positioned vertically relative to each other, each container comprising a perforated end plate and containing a portion of the biomass therein.

64. The process of claim 63, wherein the biomass in each container is compressed therein.

65. The process of claim 63, wherein the biomass is contained within the vessel at a bed porosity of at least 85 vol %.

66. The process of claim 46, further comprising:
recycling the swelling agent removed from the vessel to a second vessel containing biomass therein; and
contacting the biomass in the second vessel with the recycled swelling agent to swell or rupture at least a portion of the biomass.

67. The process of claim 66, wherein recycling the swelling agent comprises feeding the removed swelling agent to the second vessel with no processing to remove water when the removed swelling agent has a moisture content at or below a desired moisture content.

68. The process of claim 67, wherein the desired moisture content is 15 wt. %.

69. The process of claim 46, wherein removing at least a portion of the swelling agent from a first end of the vessel comprises, prior to introducing steam into the second end of the vessel, reducing pressure in the vessel to a value less than 50% of the pressure in the vessel during contacting the biomass with the swelling agent.

70. The process of claim 46, comprising performing removing at least a portion of the swelling agent and contacting the treated biomass left within the vessel with steam as a batch process.

71. The process of claim 46, comprising performing removing at least a portion of the swelling agent and contacting the treated biomass left within the vessel with steam as a continuous process.

72. The process of claim 46, comprising contacting the treated biomass left within the vessel with steam at a pressure from 5 psig to 500 psig.

73. The process of claim 46, comprising performing contacting the treated biomass left within the vessel at a temperature from 25° C. to 200° C.

74. The process of claim 46, further comprising pre-steaming the biomass in the vessel before treating the biomass with the swelling agent.

75. The process of claim 46, wherein the swelling agent is compressed vapor.

76. The process of claim 46, wherein the swelling agent is compressed ammonia.

77. The process of claim 46, wherein:
the swelling agent is ammonia, and
swelling agent is added to the vessel to provide a weight ratio of swelling agent to biomass in a contacting zone of the vessel of at least 0.1:1.

78. The process of claim 46, wherein:
the swelling agent is ammonia, and
the biomass is treated with the swelling agent to increase enzyme digestibility by at least 10% relative to that initially supplied to the vessel.

79. The process of claim 46, wherein:
the swelling agent that is removed from the vessel by contact with the steam is recovered directly from the treatment vessel during the steam contacting step, and the directly recovered swelling agent has a water content of not greater than 15 wt %, based on total content of swelling agent recovered during the steam contacting step,
the swelling agent that is removed from the vessel is removed as a vapor, and
the biomass is treated with the swelling agent to increase enzyme digestibility by at least 10% relative to that initially supplied to the vessel.

80. The process of claim 46, wherein:
the biomass is treated with the swelling agent to increase enzyme digestibility by at least 10% relative to that initially supplied to the vessel, and
the swelling agent comprises a water-soluble amine having the structure $NRR_1R_2$ where R, $R_1$ and $R_2$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

81. The process of claim 46, wherein:
the biomass is treated with the swelling agent to increase enzyme digestibility by at least 10% relative to that initially supplied to the vessel, and
the water-soluble amine is selected from the group consisting of ammonia, methylamine, dimethylamine, ethylamine, tripropylamine, morpholine, and mixtures thereof.

82. The process of claim 46, wherein:
the biomass is treated with the swelling agent to increase enzyme digestibility by at least 10% relative to that initially supplied to the vessel, and
the swelling agent comprises water-soluble ammonium ions having the structure $^+NRR_1R_2R_3$ where R, $R_1$, $R_2$, and $R_3$ are the same or different and are selected from the group consisting of H and hydrocarbons containing 1-20 carbons, optionally substituted with oxygen, nitrogen, sulfur or phosphorous, and optionally where two or more of the R groups are attached to form a cyclic group.

83. The process of claim 46, wherein:
the biomass is treated with the swelling agent to increase enzyme digestibility by at least 10% relative to that initially supplied to the vessel, and
the swelling agent comprises a hydroxide, carbonate, or bicarbonate of lithium, sodium, potassium, magnesium, or calcium.

84. The process of claim 46, wherein:
the biomass is treated with the swelling agent to increase enzyme digestibility by at least 10% relative to that initially supplied to the vessel, and
the swelling agent comprises a water soluble mono- or poly-carboxylic acid.

85. The process of claim 46, wherein:
the biomass is treated with the swelling agent to increase enzyme digestibility by at least 10% relative to that initially supplied to the vessel, and
the swelling agent comprises an inorganic acid.

86. The process of claim 46, wherein:
the biomass is treated with the swelling agent to increase enzyme digestibility by at least 10% relative to that initially supplied to the vessel, and
removing at least a portion of the swelling agent from a first end of the vessel comprises, prior to introducing steam into the second end of the vessel, reducing pressure in the vessel to a value less than 50% of the pressure in the vessel during contacting the biomass with the swelling agent.

87. The process of claim 46, wherein:
the contact of the steam and the treated biomass in the vessel is carried out to provide an Archimedes number of at least 5.0, and
the vessel includes a plurality of containers within the vessel and positioned vertically relative to each other, each container comprising a perforated end plate and containing a portion of the biomass therein.

88. The process of claim 46, wherein:
during the contact of the steam and the treated biomass in the vessel, the vessel is at a bed angle of not greater than 25 degrees from vertical, and
the vessel includes a plurality of containers within the vessel and positioned vertically relative to each other, each container comprising a perforated end plate and containing a portion of the biomass therein.

89. The process of claim 46, wherein:
the swelling agent is ammonia,
swelling agent is added to the vessel to provide a weight ratio of swelling agent to biomass in a contacting zone of the vessel of at least 0.1:1,
the swelling agent that is removed from the vessel by contact with the steam is recovered directly from the treatment vessel during the steam contacting step, and the directly recovered swelling agent has a water content of not greater than 15 wt %, based on total content of swelling agent recovered during the steam contacting step,
the steam is supplied to the vessel as saturated or superheated steam,
the biomass is treated with the swelling agent to increase enzyme digestibility by at least 10% relative to that initially supplied to the vessel, and
during the contact of the steam and the treated biomass in the vessel, the vessel is at a bed angle of not greater than 25 degrees from vertical.

\* \* \* \* \*